(12) United States Patent
Moon et al.

(10) Patent No.: US 9,421,541 B2
(45) Date of Patent: Aug. 23, 2016

(54) MICROFLUIDIC APPARATUS WITH INCREASED RECOVERY RATE OF TARGET MATERIAL FROM A SAMPLE

(71) Applicant: Samsung Electronics Co., Ltd., Suwon-si, Gyeonggi-do (KR)

(72) Inventors: Hui-sung Moon, Seoul (KR); Min-Seok S. Kim, Yongin-si (KR); Jong-myeon Park, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 237 days.

(21) Appl. No.: 14/144,165

(22) Filed: Dec. 30, 2013

(65) Prior Publication Data
US 2014/0357466 A1    Dec. 4, 2014

(30) Foreign Application Priority Data
Jun. 4, 2013   (KR) ........................ 10-2013-0064318

(51) Int. Cl.
| | | |
|---|---|---|
| *B01L 3/00* | (2006.01) | |
| *G01N 1/40* | (2006.01) | |
| *B04B 5/04* | (2006.01) | |
| *B04B 7/02* | (2006.01) | |
| *B04B 11/00* | (2006.01) | |
| *G01N 35/00* | (2006.01) | |

(52) U.S. Cl.
CPC .... *B01L 3/502715* (2013.01); *B01L 2200/027* (2013.01); *B01L 2300/041* (2013.01); *B01L 2300/0803* (2013.01); *B01L 2300/0887* (2013.01); *B01L 2400/0409* (2013.01); *B01L 2400/0677* (2013.01); *B01L 2400/0683* (2013.01); *B04B 5/0407* (2013.01); *B04B 7/02* (2013.01); *B04B 11/00* (2013.01); *G01N 1/4077* (2013.01); *G01N 2035/00495* (2013.01)

(58) Field of Classification Search
CPC .......... B04B 5/0407; B01L 3/502715; B01L 2200/027; B01L 2300/041; B01L 2300/0803; B01L 2300/0887; B01L 2400/0409; B01L 2400/0677; B01L 2400/0683; G01N 1/4077; G01N 2035/00495
USPC ..................................... 494/37, 43
See application file for complete search history.

(56) References Cited

U.S. PATENT DOCUMENTS 7,988,915 B2 * 8/2011 Lee ................... B01L 3/502738
                                                    422/500
8,367,398 B2    2/2013 Lee et al.
(Continued)

FOREIGN PATENT DOCUMENTS

| EP | 2000210 A1 * | 12/2008 | .......... B01L 3/50273 |
|---|---|---|---|
| EP | 2026074 A2 * | 2/2009 | .......... B01F 11/0002 |
| KR | 2011/0057416 A | 6/2011 | |

*Primary Examiner* — Charles Cooley
*Assistant Examiner* — Shuyi S Liu
(74) *Attorney, Agent, or Firm* — Leydig, Voit & Mayer, Ltd.

(57) ABSTRACT

A microfluidic apparatus that is mounted on a rotation driver and induces a flow of a fluid according to a centrifugal force includes a lower structure having a microfluidic structure including a recovery chamber for accommodating a target material separated from a sample and a channel for forming an inflow path of the target material to the recovery chamber; an upper plate forming an upper wall of the recovery chamber and the channel; and a lid formed integrally to the upper plate and removable from the upper plate to open at least a part of a top of the recovery chamber.

17 Claims, 10 Drawing Sheets

(56) References Cited

U.S. PATENT DOCUMENTS

| | | | |
|---|---|---|---|
| 2001/0048895 A1 | 12/2001 | Virtanen | |
| 2003/0044853 A1* | 3/2003 | Socks | G01N 33/5008 435/7.9 |
| 2007/0125942 A1* | 6/2007 | Kido | B01F 13/0059 250/284 |
| 2009/0143250 A1* | 6/2009 | Lee | B01L 3/502738 506/39 |
| 2009/0238724 A1 | 9/2009 | Yamamoto et al. | |
| 2011/0041922 A1* | 2/2011 | Ussing | B01L 3/502715 137/13 |
| 2011/0232832 A1* | 9/2011 | Park | F16K 99/0001 156/155 |
| 2012/0184010 A1 | 7/2012 | Medoro et al. | |

* cited by examiner

US 9,421,541 B2

MICROFLUIDIC APPARATUS WITH INCREASED RECOVERY RATE OF TARGET MATERIAL FROM A SAMPLE

CROSS-REFERENCE TO RELATED APPLICATIONS

This application claims the benefit of Korean Patent Application No. 10-2013-0064318, filed on Jun. 4, 2013, in the Korean Intellectual Property Office, the disclosure of which is incorporated herein in its entirety by reference.

BACKGROUND

1. Field

The present disclosure relates to microfluidic apparatuses for inducing a flow of a fluid according to a centrifugal force, and separating and recovering a target material from a sample in a fluid form.

2. Description of the Related Art

Most malignant tumor-related deaths are caused by metastasis to a tissue or organ located away from a point where a tumor originated. Thus, the discovery of metastasis at an early stage is a critical factor that determines the survival probability of a cancer patient. Early detection and monitoring a growth of a tumor are deemed to be key factors in successfully treating cancer patients. A histopathology-based diagnosis is usually used to detect a cancer. The histopathology-based diagnosis is a method of diagnosing a tumor by using a tissue sample obtained from a biopsy specimen. According to the histopathology-based diagnosis, a tumor cell is directly observed. However, a biopsy specimen only provides information about the tissue contained in the biopsy specimen, and thus, a biopsy specimen may not generally be used to identify tumor metastasis. Accordingly, the use of histopathology in diagnosing or monitoring tumors, especially metastasized tumors, has many limitations Circulating tumor cells (CTCs) may be identified in patients before a tumor is originally detected. Thus, CTCs may play an important factor in early diagnosing of a cancer. In addition, since a cancer may spread through blood, CTCs may be considered as a marker for identifying cancer metastasis. In addition, when CTCs are detected after a tumor is removed by a surgical operation, the possibility of recurrence of a cancer is very high. However, since the amount of CTCs in blood may be very small and since CTCs are very fragile, it is difficult to correctly quantify CTCs. Accordingly, there is a need to develop a diagnosis method having high sensitivity in detecting CTCs, cancer cells, or cancer stem cells present in the body of patients.

Red blood cells, white blood cells/circulating cancer cells, or serums may be manually separated based on a density gradient of a layer in order to isolate CTCs, cancer cells, or cancer stem cells. However, a layer of white blood cells/circulating cancer cells is very thin, and thus, manually separating the layer of white blood cells/circulating cancer cells based on the density gradient is difficult, and also, the separation reproducibility largely depends on the ability of a person who performs the separation.

SUMMARY

Provided is a microfluidic apparatus capable having an increased recovery rate of a target call separated from a sample.

According to an aspect of the present inventive concept, a microfluidic apparatus that may be mounted on a rotation driver to induce a flow of a fluid according to a centrifugal force, the microfluidic apparatus includes: a lower structure having a microfluidic structure including a recovery chamber for accommodating a target material separated from a sample and a channel for forming an inflow path of the target material to the recovery chamber; an upper plate forming an upper wall of the recovery chamber and the channel; and a lid formed integrally with the upper plate and removable from the upper plate to open at least a part of a top of the recovery chamber.

The microfluidic apparatus is configured to be rotated on a rotational driver. Thus, the apparatus may have a point of rotation by which the apparatus is rotated on a rotational axis. As illustrated in the Figures, the upper plate and lower structure generally have a width (dimension perpendicular to the rotational axis) that is greater than their thickness or depth (dimension parallel to the rotational axis).

The upper plate may include a removal groove that is depressed into the upper plate (e.g., recessed from a top surface and/or a bottom surface of the upper plate), which removal groove defines an edge of the lid and defining at least a portion of the perimeter of the lid. The removal groove serves as a breakage line, such that the lid may be separated from the upper plate along the removal groove.

A part of the edge of the lid may be exposed along the outside edge or perimeter of the microfluidic apparatus. For instance, when the apparatus takes the form of a disc, the lid is integrated into the upper plate at a position such that a portion of the lid is part of (and, thus, exposed along) the outer perimeter edge of the apparatus (outer perimeter edge of the upper plate). In this way, an edge of the lid is accessible to facilitate removal of the lid.

To further facilitate removal of the lid, the lower structure of the apparatus may comprise a depression in an outer perimeter of the lower structure adjacent to the portion of the lid exposed along the outer perimeter of the apparatus. The depression is, thus, in a region of the lower structure corresponding to the exposed part of the edge of the lid. The depression may be depressed from a top surface (adjacent the upper plate) of this region of the lower structure, and extend inward from the perimeter of the apparatus towards the center of the apparatus and along a bottom surface of the lid. In this way, the depression may expose a portion of the bottom surface of the lid adjacent the lower structure, and provide an access point by which a lever may be inserted to assist in detaching the lid from the upper plate.

The recovery chamber may include a first region facing the channel and a second region located outside the first region in a circumferential direction, and the lid may open a top of the second region. In other words, the lid may be positioned to cover only a portion of the recovery chamber that is offset in a circumferential direction from an inlet of the channel into the recovery chamber. The second region may have a depth that is smaller than the depth of the first region. Thus, the portion of the recovery chamber covered by the lid may have less depth than the portion of the recovery chamber that is not offset in a circumferential direction from an inlet of the channel into the recovery chamber (e.g., a portion that is covered by the upper plate but not the lid). A depth of the recovery chamber may gradually decrease from the first region to the second region.

The apparatus may include a first lid and a second lid that are spaced apart from each other. The recovery chamber may include a first region facing the channel and a second region, as described above, located on both sides of the first region (i.e., flanking the first region) in a circumferential direction, and the first and second lids may open a top of the second region when removed from the upper plate. Thus, the first and second lids may be positioned to cover only portions of the recovery chamber that are offset in a circumferential direction from an inlet of the channel into the recovery chamber.

All aspects of the second lid may otherwise be the same as described for the first lid (referred to simply as "the lid"). Thus, for instance, the upper plate may include first and second removal grooves defining the first and second lids by being depressed into the upper plate from a top surface or a bottom surface of the upper plate such that the first and second lids are integrally formed with the upper plate, and the first and second lids may be separated from the upper plate along the first and second removal grooves. Also, parts of edges of the first and second lids may be exposed outside the microfluidic apparatus. The microfluidic apparatus may further include first and second depressed portions extending inward from the exposed parts of the first and second lids along bottom surfaces of the first and second lids.

The recovery chamber may include a first region facing the channel and a second region located outside the first region in a circumferential direction, and a depth of the second region may be smaller than a depth of the first region. Thus, the portions or regions of the recovery chamber covered by the first and/or second lids may have a depth that is less than the depth of the first region that is not offset from the inlet of the channel into the recovery chamber and is not covered by the first or second lids. A depth of the recovery chamber may gradually decrease from the first region to the second region.

The microfluidic apparatus may further include: a sample chamber in which fine beads are adhered to a target cell in the sample to form the target material; and a separation chamber for accommodating a density gradient medium having a lower density than the target material, receiving a fluid including the target material from the sample chamber, and separating the target material from the fluid according to a density difference. The target cell may be a circulating tumor cell, a cancer stem cell, or a cancer cell.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
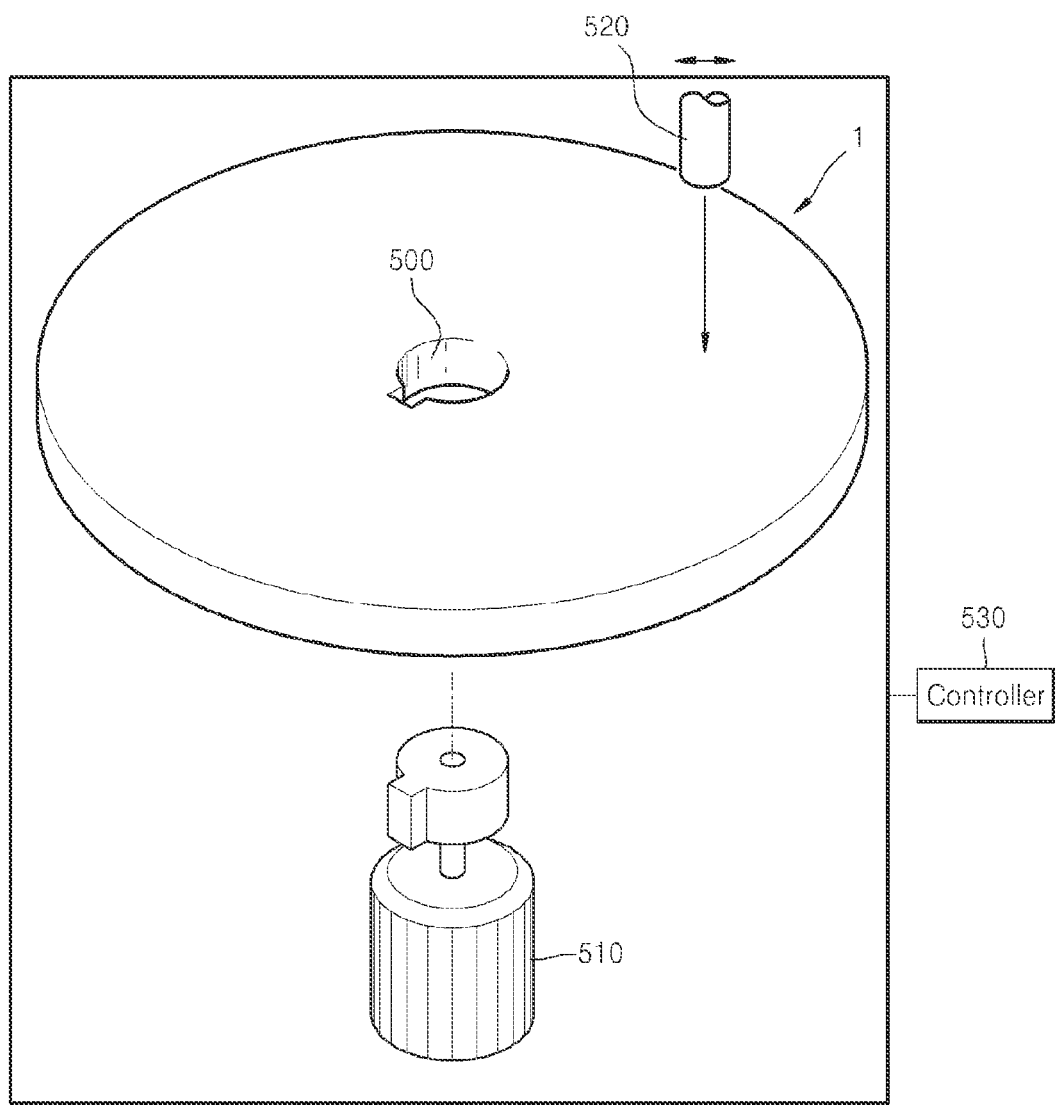
FIG. 1 is a schematic diagram of a target cell enrichment system.

Reference will now be made in detail to embodiments, examples of which are illustrated in the accompanying drawings, wherein like reference numerals refer to like elements throughout. In this regard, the current embodiments may have different forms and should not be construed as being limited to the descriptions set forth herein. Accordingly, the embodiments are merely described below, by referring to the figures, to explain aspects of the present description.

FIG. 1 is a schematic diagram of a target cell enrichment system using a microfluidic apparatus 1. Referring to FIG. 1, the target cell enrichment system includes a rotation driver 510 and an electromagnetic wave generator 520. The rotation driver 510 rotates the microfluidic apparatus 1 to provide a centrifugal force for centrifugation of a sample and movement of a fluid. The rotation driver 510 stops the microfluidic apparatus 1 at a predetermined location so that valves face the electromagnetic wave generator 520. The electromagnetic wave generator 520 operates the valves of the microfluidic apparatus 1, e.g., by irradiating laser beams. The electromagnetic wave generator 520 may move in a radial direction of the microfluidic apparatus 1. The rotation driver 510 may include a motor drive device (not shown) that controls an angular position of the microfluidic apparatus 1 so as to align the valves with the electromagnetic wave generator 520. For example, the motor drive device may be a step motor or a direct current (DC) motor. Reference numeral 530 denotes a controller for controlling an enrichment process.

Figure 2:
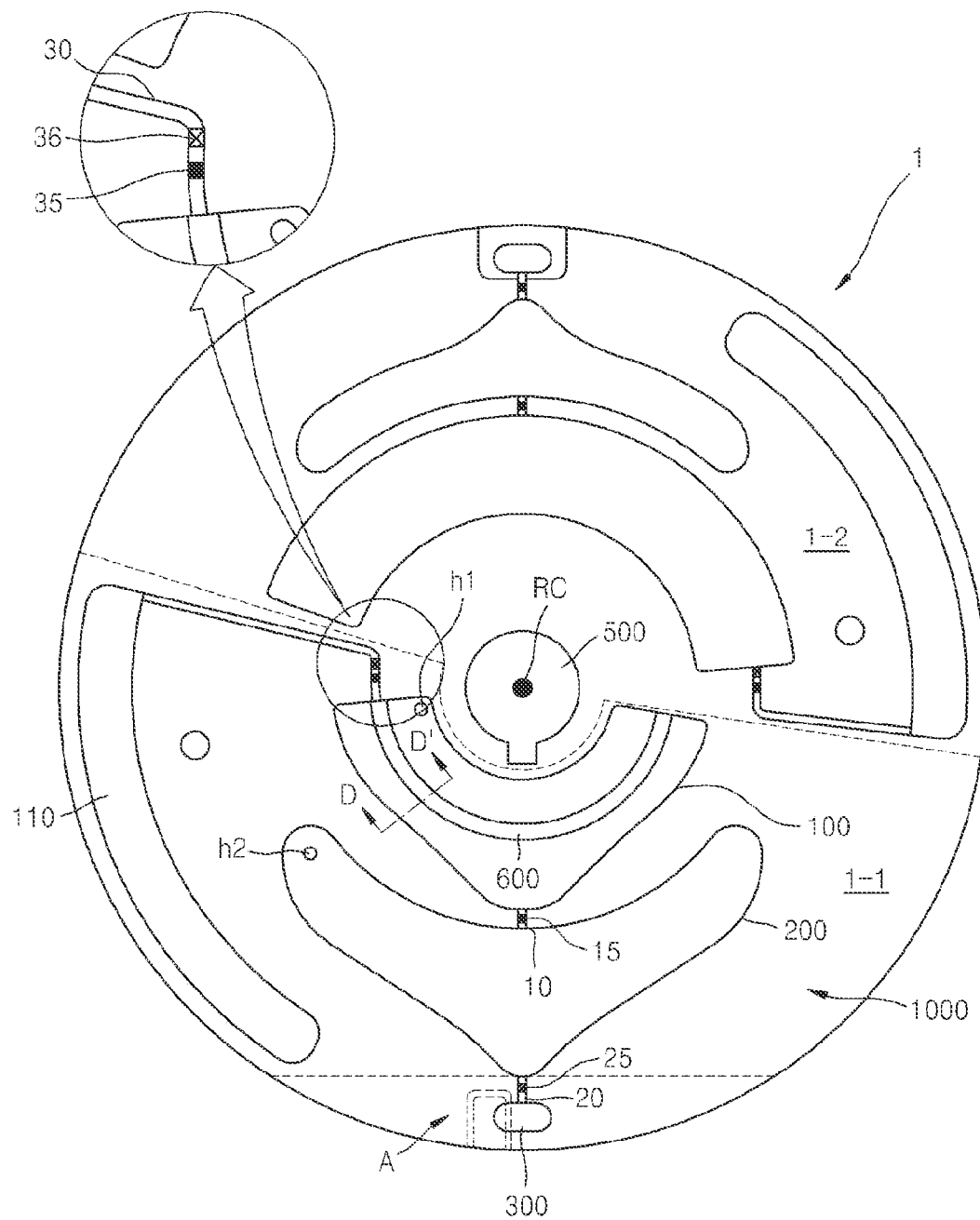
FIG. 2 illustrates a configuration of a microfluidic apparatus.

FIG. 2 illustrates a configuration of the microfluidic apparatus 1 according to an embodiment of the present inventive concept. The microfluidic apparatus 1 includes a microfluidic structure including a chamber for accommodating the fluid and a channel for providing a fluid path. The microfluidic apparatus 1 may have a rotatable disk shape, but is not limited thereto.

The microfluidic apparatus 1 may include a lower structure having the microfluidic structure, wherein chambers forming accommodation spaces for the fluid and a channel providing a fluid path between the chambers are engraved, and an upper structure (an upper plate) forming an upper wall of the microfluidic structure by being bonded to the lower structure. The microfluidic apparatus 1 may have a two-plate structure, wherein an upper plate and a lower plate having the microfluidic structure are bonded. Alternatively, the microfluidic apparatus 1 may have a three-plate structure, wherein a partition plate for defining the microfluidic structure is disposed between an upper plate and a lower plate. Plates may be bonded by using any one of various methods, such as bonding using an adhesive or a dual adhesive tape, and welding using ultrasonic waves or laser beams.

The microfluidic apparatus 1 may be formed of a plastic material such as acryl or polydimethylsiloxane (PDMS), which is molded easily and has a biologically inactive surface. However, a material of the microfluidic apparatus 1 is not limited thereto, and the microfluidic apparatus 1 may be formed of any material having chemical and biological stability, optical transparency, and mechanical processability.

The microfluidic apparatus 1 may include one or more microfluidic structures. For example, the microfluidic apparatus 1 may be divided into a plurality of regions, each region having a microfluidic structure that operates independently from one another. In the microfluidic apparatus 1 according to the current embodiment, the microfluidic structures are provided in two regions 1-1 and 1-2. Since the microfluidic structures provided in the two regions 1-1 and 1-2 are substantially the same, only the microfluidic structure in the region 1-1 will be described in more detail.

Referring to FIG. 2, the microfluidic apparatus 1 has a mounting portion 500 at its rotation center RC in order to be mounted onto the rotation driver 510. The microfluidic apparatus 1 includes a separation unit 1000 and a recovery chamber 300. The separation unit 1000 separates a target cell from a biological sample using a centrifugal force. The recovery chamber 300 is disposed outside the separation unit 1000 in the radial direction based on the rotation center RC and collects the target cell.

The separation unit 1000 may include a sample chamber 100 and a separation chamber 200 connected to each other through a sample channel 10. The separation chamber 200 is connected to the recovery chamber 300 through a recovery channel 20. A sample valve 15 and a recovery valve 25 for controlling the flow of the fluid are disposed in the sample channel 10 and the recovery channel 20, respectively.

The sample chamber 100 supplies a sample containing a target material, e.g., a target cell-fine bead complex. In the sample chamber 100, a target cell and fine beads contained in the sample contact each other, and the fine beads adhere to the target cell to form the target cell-fine beads complex. For example, the fine beads may be solid microbeads, magnetic beads, gel beads, or polymer microbeads. In one embodiment, the sample chamber 100 may include an inlet hole h1 through which a sample is loaded. The fine beads may be loaded into the sample chamber 100 through the inlet hole h1 prior to separation of the target cell from the sample. The inlet hole h1 may be formed in an upper plate (not shown). When the microfluidic apparatus 1 is manufactured for a predetermined task, fine beads suitable for the task may be introduced in the sample chamber 100 during the manufacturing of the microfluidic apparatus 1.

The target cell may be a circulating tumor cell (CTC), a cancer stem cell, or a cancer cell. For example, the target cell may be a cancer cell or tumor cell from any type of cancer, for instance, bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal cancer, ovarian cancer, pancreatic cancer, gallbladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, adult T-cell leukemia, lymphoma, multiple myeloma, glioblastoma/astrocytoma, melanoma, mesothelioma, or Wilms' tumor, but not limited thereto.

The sample may include any of a number of biological samples as long as the target cell exists therein. For example, the biological sample may be a biopsy sample, a tissue sample, a cell suspension having a separated cell suspended in a liquid medium, a cell culture, and any combinations thereof, without limitation. The sample may also be selected from the group consisting of blood, marrow fluid, saliva, lacrimal fluid, urine, semen, mucous fluid, and any combinations thereof. For example, in order to separate CTCs, blood may be used as the sample.

At least one ligand specific to a surface marker of a target cell is bonded to the fine beads. The fine beads serve to increase a density of the target cell by bonding to the target cell. The fine beads may have a density value which may cause a density difference between the target cell and another cell in the sample. For example, when a biological sample is blood containing a cancer cell as the target cell, since white blood cells (WBCs) and red blood cells (RBCs) have densities of about 1.07 $g/cm^3$ and about 1.1 $g/cm^3$, respectively, fine beads with an appropriate density may be selected in consideration of such densities. For example, the fine beads may be polystyrene particles, polymethylmethacrylate particles, latex particles, acrylonitril-butadiene-styrene copolymer (ABS) particles, or a complex thereof, but the beads are not limited thereto. A diameter of the fine beads may vary according to a type of the target cell to be separated and a type of beads to be used. The diameter may be, for example, from about 1 nm to about 100 μm, or from about 10 nm to about 10 μm.

The surface marker may be any marker, such as protein, sugar, lipid, nucleic acid, or any combinations thereof. For example, the surface marker may be a protein, e.g., an antigen, which is specifically expressed in a cancer or tumor cell and is displayed in a cell membrane, such as epithelial cell adhesion molecule (EpCAM), c-Met, cytokeratines, CD45, Human Epidermal Growth Factor Receptor 2 (Her2), or any combinations thereof. In addition, the at least one ligand specific to the surface marker may be an antibody that binds specifically to an antigenic protein.

The separation chamber 200 separates a target material from a sample supplied from the sample chamber 100 and accommodates a density gradient medium (DGM). The DGM is used to separate a target material from a sample by using a density gradient. The DGM has a lower density than that of the target material and a greater density than that of the fluid excluding the target material. Thus, during centrifugation, the DGM is interposed between the fluid and the target material so as to separate the target material from the fluid. The separation chamber 200 may include an inlet hole h2 through which the DGM is loaded. The inlet hole h2 may be formed in an upper plate (not shown). When the microfluidic apparatus 1 is to be used for a particular task, a DGM suitable for the particular task may be accommodated in the separation chamber 200 in advance, for example, during the manufacturing of the microfluidic apparatus 1.

The separation chamber 200 is disposed outside the sample chamber 100 in the radial direction based on the rotation center RC so that the sample flows from the sample chamber 100 to the separation chamber 200 according to a centrifugal force. In other words, the separation chamber 200 is located farther from the RC than the sample chamber 100, and may be generally aligned with the sample chamber 100 in a radial direction from the RC, such that the sample chamber 100 is positioned generally between the RC and the separation chamber 200. The separation chamber 200 is connected to the sample chamber 100 by channel 10. In the separation chamber 200, the target material and the fluid are separated from each other by the DGM interposed therebetween. The target material is collected into a lowermost layer of the separation chamber 200, that is, a most outside material layer in the radial direction based on the rotation center RC.

The recovery chamber 300 is disposed outside the separation chamber 200 in the radial direction based on the rotation center RC. In other words, the recovery chamber 300 is located farther from the RC than the separation chamber 200, and may be generally aligned in a radial direction with the separation chamber 200, such that the separation chamber 200 is generally positioned between the recovery chamber 300 and the sample chamber 100. The recovery chamber 300 is connected to the separation chamber 200 via the recovery channel 20. In the separation chamber 200, the target material is collected into the lowermost region or layer of the separation chamber 200. When the recovery channel 20 is opened by the recovery valve 25, the target material is introduced into the recovery chamber 300 according to a centrifugal force.

As shown in FIG. 2, the separation unit 1000 may further include a waste chamber 110 disposed outside the sample chamber 100 in the radial direction based on the rotation center RC. The waste chamber 110 is also connected to the sample chamber 100 through a discharge channel 30. Discharge valves 35 and 36 are disposed in the discharge channel 30 to control the flow of the fluid.

Before forming the target material in the sample chamber 100, a portion of the sample in the sample chamber 100 may be removed. For example, after performing centrifugation on the sample in the sample chamber 100, an upper material layer located at an upper portion of the target cell in the sample chamber 100 is discharged to the waste chamber 110. Then, fine beads and the sample are mixed to bond the target cell and the fine beads, thereby forming the target material. If blood containing circulating cancer cells is subjected to centrifugation within the sample chamber 100, a plasma layer may be separated as an uppermost layer that is closest to the rotation center RC, and may be pumped into the waste chamber 110. Protein contained in the plasma layer may bond to the fine beads, thereby deteriorating a bonding rate of the circulating cancer cells and the fine beads, and thus, the plasma layer may be removed to improve the bonding efficiency between the fine beads and the circulating cancer cells.

The sample valve 15, the recovery valve 25, and the discharge valves 35 and 36 may be microfluidic valves. The sample valve 15 and the discharge valve 35 may be normally closed valves that close the sample channel 10 and the discharge channel 30 in a normal state, and open the sample channel 10 and the discharge channel 30 upon receiving energy from the outside. The recovery valve 25 and the discharge valve 36 are open valves that open the recovery channel 20 and the discharge channel 30 when they are in a normal state, and close the recovery channel 20 and the discharge channel 30 upon receiving energy from outside the apparatus.

Figure 3A:
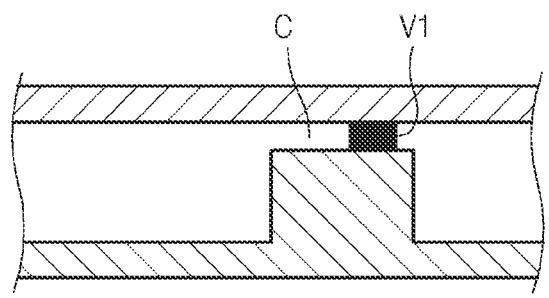
FIGS. 3A and 3B are cross-sectional views of a normally closed valve.
Figure 3B:
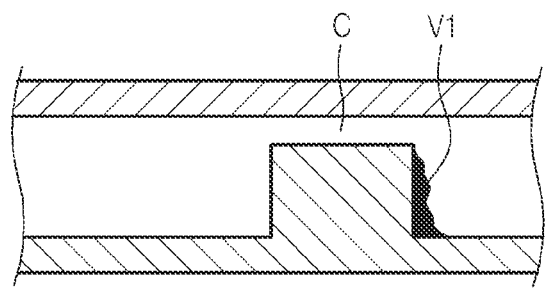

FIGS. 3A and 3B are cross-sectional views of a normally closed valve according to an embodiment of the present inventive concept. The normally closed valve may include a valve material V1 that is in a solid state at room temperature. The valve material V1 exists in a channel C in the solid state to block the channel C as shown in FIG. 3A. The valve material V1 melts at a high temperature upon receiving external energy and moves to a space in the channel C, and then coagulates again while the channel C is opened as shown in FIG. 3B.

Figure 4A:
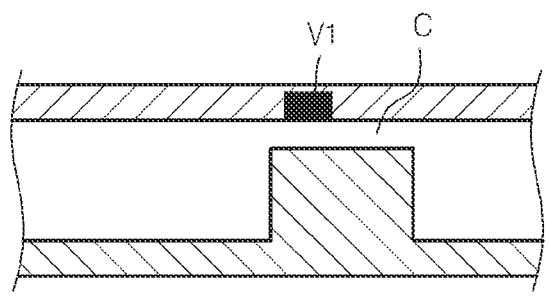
FIGS. 4A and 4B are cross-sectional views of a normally opened valve.
Figure 4B:
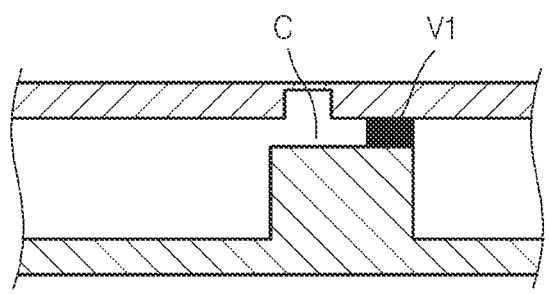

FIGS. 4A and 4B are cross-sectional views of a normally opened valve according to an embodiment of the present inventive concept. The normally opened valve may include the valve material V1 in a solid state. The valve material V1 exists on the channel C in the solid state, and the channel C maintains an opened state as shown in FIG. 4A. The valve material V1 melts at a high temperature upon receiving external energy and moves to the space in the channel C, and then coagulates to close the channel C as shown in FIG. 4B.

The external energy may be, for example, electromagnetic waves, and an external energy source may be a laser light source emitting laser beams, or a light emitting diode or Xenon lamp emitting visible rays or infrared rays. When the external energy source is the laser light source, it may include at least one laser diode. The external energy source may be selected according to a wavelength of the electromagnetic waves that may be absorbed by exothermic particles contained in the valve material V1. The valve material V1 may be a thermoplastic resin such as cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF). Alternatively, a phase change material that is in a solid state at room temperature may be used as the valve material V1. The phase change material may be wax. When the wax is heated, the wax melts into a liquid state and expands. The wax may be paraffin wax, microcrystalline wax, synthetic wax, or natural wax. The phase change material may be a gel or thermoplastic resin. The gel may be polyacrylamides, polyacrylates, polymethacrylates, or polyvinylamides. In the valve material V1, a plurality of fine exothermic particles which absorb electromagnetic wave energy to generate heat may be dispersed. Each of the fine exothermic particles may have a diameter of about 1 nm to about 100 μm so as to freely pass through the channel C having a depth of about 0.1 mm and a width of about 1 mm. When the electromagnetic wave energy is supplied to the fine exothermic particles through laser beams, for example, the temperature of the fine exothermic particles rises rapidly to generate heat, and the fine exothermic particles are evenly dispersed in the wax. The fine exothermic particles may have a core containing a metal component, and a hydrophobic surface structure. For example, the fine exothermic particles may have a molecular structure including a core formed of iron (Fe) and a plurality of surfactants that are bonded to and surround Fe. The fine exothermic particles may be dispersed and stored in carrier oil. The carrier oil may also be hydrophobic so that the fine exothermic particles having a hydrophobic surface structure may be evenly dispersed. The carrier oil in which the fine exothermic particles are dispersed is mixed into the melted phase change material, and the mixture is injected into the channel C and solidified to block the channel C. The fine exothermic particles are not limited to the above-described polymer particles, and may be quantum dots or magnetic beads. Alternatively, the fine exothermic particles may be fine metal oxides such as aluminum oxide ($Al_2O_3$), titanium oxide ($TiO_2$), tantalum oxide ($Ta_2O_3$), iron oxide ($Fe_2O_3$), $Fe_3O_4$, or hafnium oxide ($HfO_2$). On the other hand, the normally closed valve does not necessarily include the fine exothermic particles, and may be formed of the phase change material only without the use of the fine exothermic particles.

Figure 5:
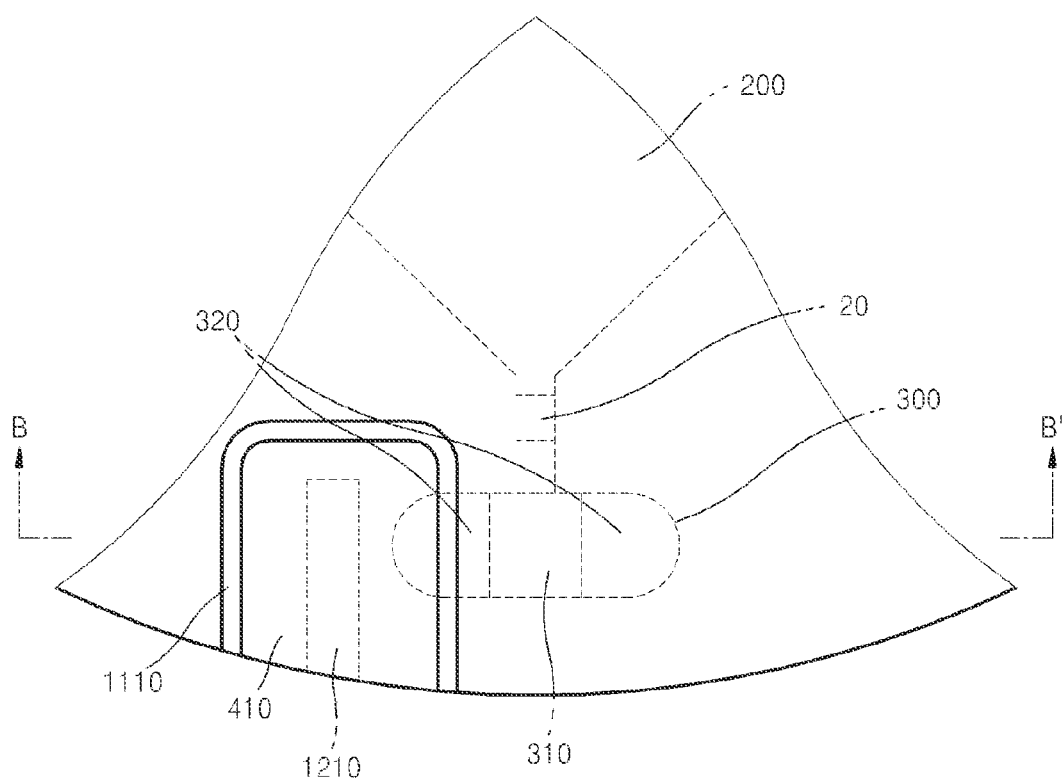
FIG. 5 is a detailed partially exploded perspective view of portion A of the microfluidic apparatus of FIG. 2.
Figure 6:
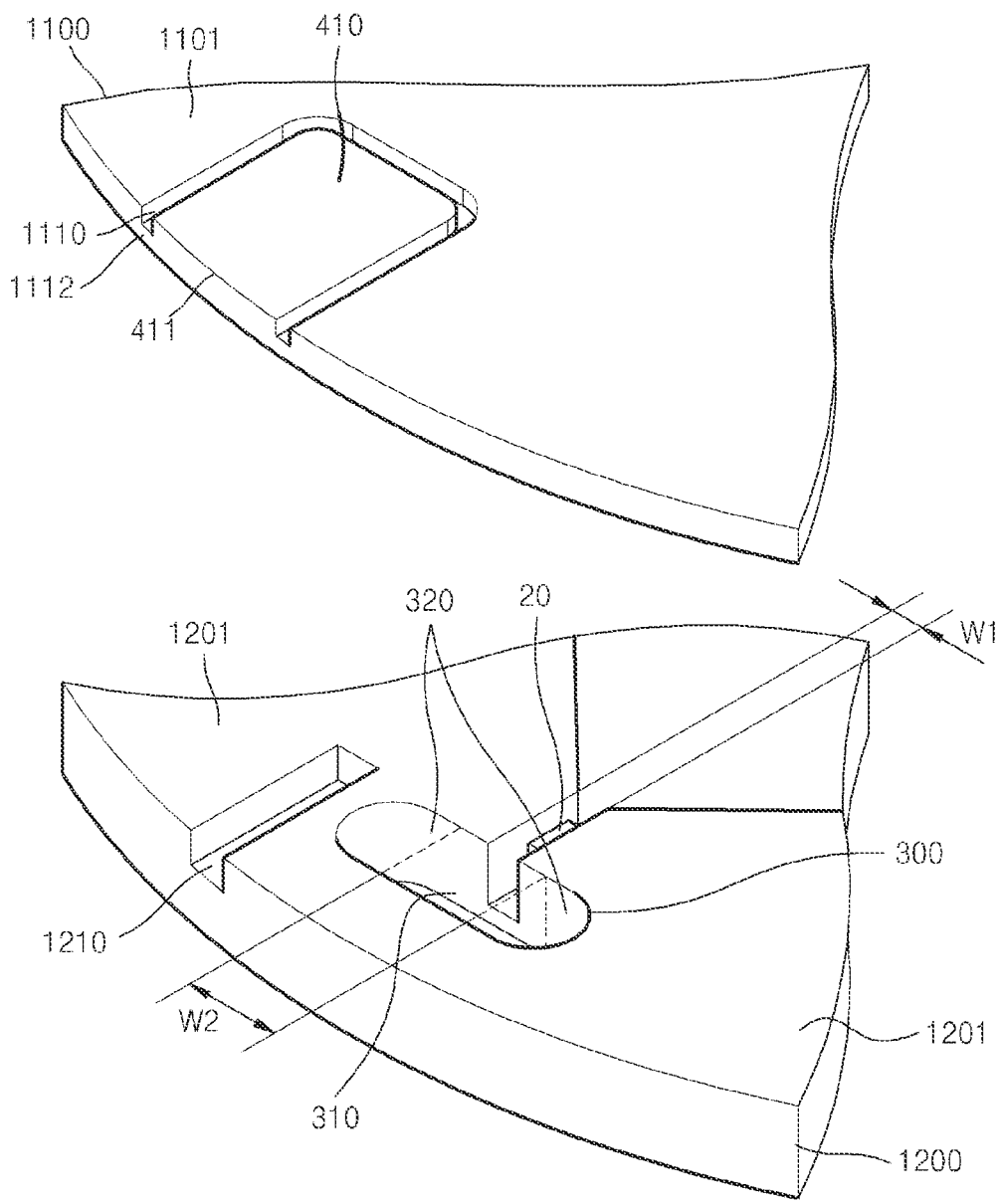
FIG. 6 is an exploded perspective view of portion A of the microfluidic apparatus of FIG. 2.
Figure 7:
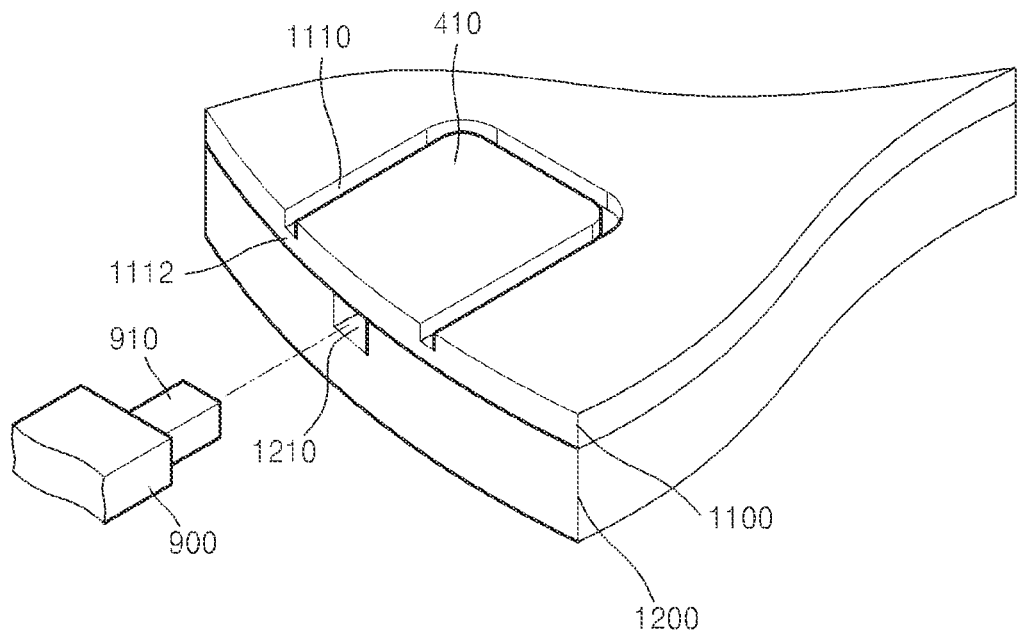
FIG. 7 is a perspective view of portion A of the microfluidic apparatus of FIG. 2.
Figure 8:
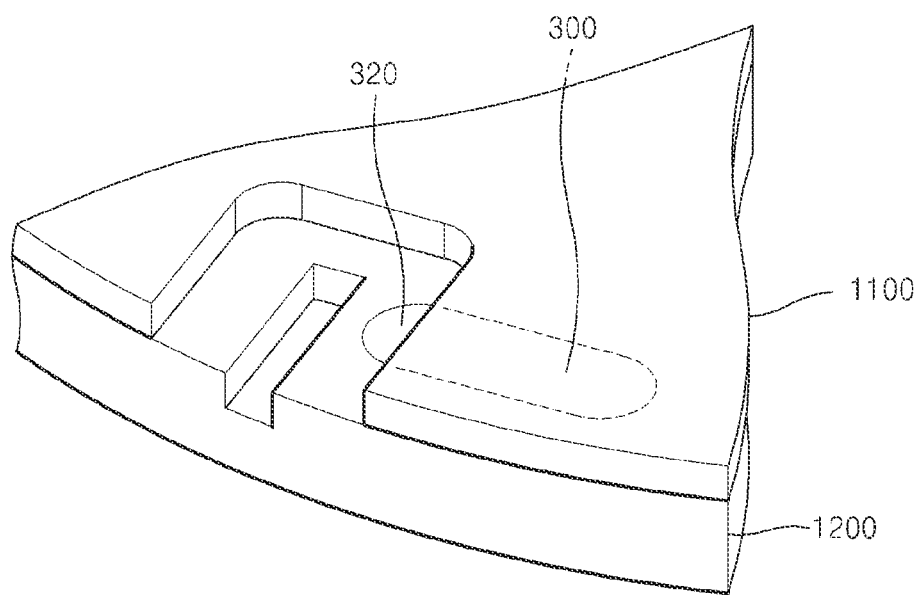
FIG. 8 is a perspective view of portion A of the microfluidic apparatus of FIG. 2, not including a lid.

FIG. 5 is a detailed partial exploded perspective view of a portion A of FIG. 2. FIG. 6 is an exploded perspective view of FIG. 5. FIG. 7 is a perspective view of FIG. 5. FIG. 8 is a perspective view of FIG. 5, not showing a first lid 410. Referring to FIGS. 5 and 6, the microfluidic apparatus 1 may include a lower structure 1200 having a microfluidic structure in which the recovery chamber 300, the separation chamber 200, the recovery channel 20, the sample chamber 100, the waste chamber 110, the sample channel 10, and the discharge channel 30 are engraved (not shown in FIGS. 5 through 8), and an upper plate 1100 forming an upper wall of the microfluidic structure. A first lid 410 for opening the top of the recovery chamber 300 is integrally formed to the upper plate 1100.

According to an embodiment, the upper plate 1100 has a first removal groove 1110 that is depressed into the upper plate 1100 from at least one of a bottom surface and a top surface of the upper plate 1100 along an edge of the first lid 410. In this embodiment, first removal groove 1110 is depressed downward from a top surface 1101 of the upper plate 1100 along an edge of the first lid 410. A part 411 of the edge of the first lid 410 is exposed outside the microfluidic apparatus 1. In other words, the part 411 of the edge of the first lid 410 is formed along an outer edge of the microfluidic apparatus 1. Accordingly, the first removal groove 1110 has an overall "U" shape when viewed top-down in the direction parallel to the rotational axis. A first connecting portion 1112 connecting the upper plate 1100 and the first lid 410 is formed by the first removal groove 1110.

A region of the lower structure 1200 corresponding to the exposed part 411 of the first lid 410 has a first depressed portion 1210 that extends inward along a bottom surface of the first lid 410 by being depressed from a top surface 1201 of the lower structure 1200. An end portion of the first depressed portion 1210 is externally exposed when the upper plate 1100 and the lower structure 1200 are combined, and thus a gap is formed between the first lid 410 and the lower structure 1200. For example, as shown in FIG. 7, when an insertion protrusion 910 of a separation tool 900 is inserted into the first depressed portion 1210 and lifted upward, the connection portion 1112 having a relatively thin thickness is broken and the first lid 410 is separated from the upper plate 1100. Accordingly, a part of the top of the recovery chamber 300 may be opened as shown in FIG. 8.

In conventional devices, an outlet hole (not shown) may be prepared in a region of the upper plate 1100 corresponding to the top of the recovery chamber 300 through which target materials are recovered. While the target material is separated, the outlet hole may be blocked by using an adhesive tape or the like, and after the target material is separated, the outlet hole may be opened and the target material may be recovered through the outlet hole by using a pipette or the like. However, since a size of the outlet hole is generally very small, it is not easy to recover the target material by using the pipette. Also, since the adhesive tape may be damaged due to a strong centrifugal force while separating the target material, the size of the outlet hole is difficult to be increased.

According to the current embodiment, the first lid 410 is integrally formed to the upper plate 1100, and the first lid 410 is removed to open the top of the recovery chamber 300 after the separation of the target material. Accordingly, the top of the recovery chamber 300 may be relatively largely opened without damaging the first lid 410 during the separation of the target material, and thus a recovery rate of the target material may be increased. A number of components may be reduced by integrally forming the first lid 410 to the upper plate 1100, and since the upper plate 1100 and the first lid 410 are manufactured by using one mold, component costs and manufacture costs may be reduced.

Referring back to FIGS. 5 and 6, the recovery chamber 300 may include a first region 310 facing the recovery channel 20, and a second region 320 disposed outside the first region 310 in a circumferential direction (e.g., the second region is adjacent to or flanking the first region 310 in a direction along the circumference or periphery of the apparatus). The first lid 410 may be disposed in the upper plate to cover a portion of the second region 320, such that removal of the lid opens the top of the second region 320, and does not cover the first region 310. In other words, the lid covers only a portion of the recovery chamber that is offset in a circumferential direction (in the direction along the circumference or periphery of the device) from the entrance (inlet or junction) of the channel into the recovery chamber. A width W2 of the first region 310 may be equal to or larger than a width W1 of the recovery channel 20.

The target material is transported from the separation chamber 200 to the recovery chamber 300 through the recovery channel 20 according to a centrifugal force generated by rotation of the microfluidic apparatus 1. The target material is mainly collected in the first region 310. The target material that passed through the recovery channel 20 is introduced into the recovery chamber 300 according to a strong centrifugal force, and the recovery channel 20 is located above the bottom of the recovery chamber 300. If the first lid 410 is located above the first region 310, the target material that passed through the recovery channel 20 is attached to the bottom surface of the first lid 410. As a result, when the first lid 410 is removed, the target material is removed together with the first lid 410, and thus, a recovery rate of the target material may be deteriorated. According to the microfluidic apparatus 1 of the current embodiment, since the first lid 410 opens the top of the second region 320, the target material is less likely to be attached to the bottom surface of the lid and a loss of the target material is reduced, thereby improving the recovery rate of the target material.

Figure 9:
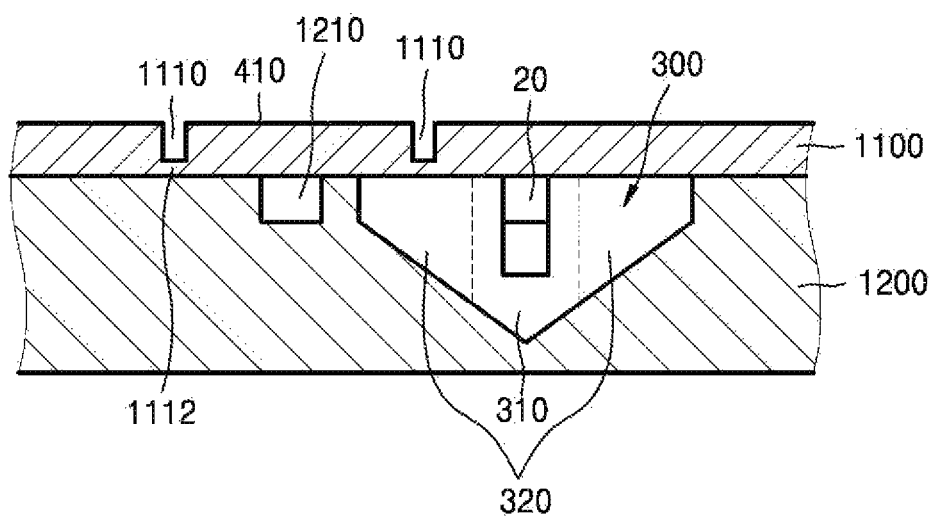
FIG. 9 is a cross-sectional view taken along line B-B' of FIG. 5.
Figure 10:
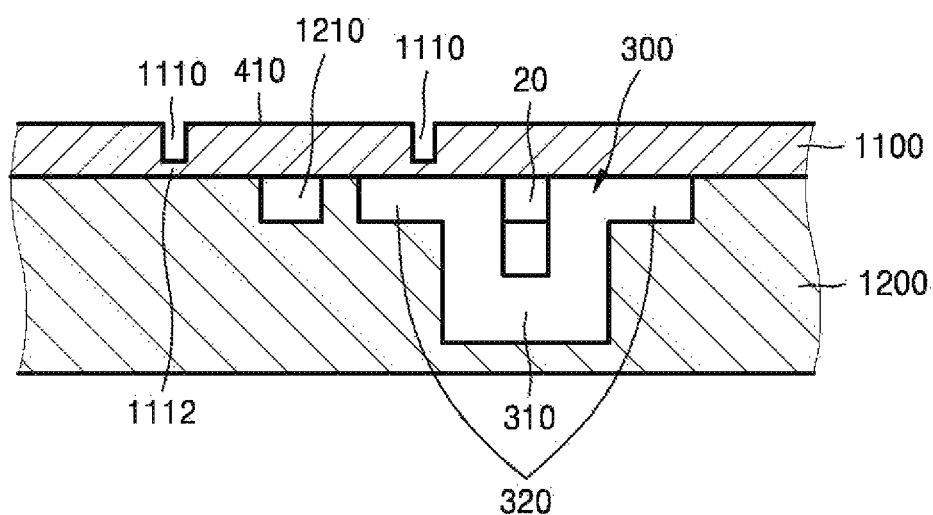
FIG. 10 is a cross-sectional view taken along line B-B' of FIG. 5.

FIG. 9 is a cross-sectional view taken along a line B-B' of FIG. 5. Referring to FIG. 9, a depth of the second region 320 is smaller than a depth of the first region 310 in the recovery chamber 300, wherein depth refers a dimension of the chamber in a direction parallel to the axis of rotation. The target material introduced into the recovery chamber 300 is mainly collected in the first region 310 that is relatively deep, and rarely moves to the second region 320 that is relatively shallow. Accordingly, a possibility that the target material is attached to the bottom surface of the first lid 410 on the second region 320 may be reduced, thereby increasing the recovery rate of the target material. As shown in FIG. 9, the recovery chamber 300 may have a shape where a depth gradually decreases from the first region 310 to the second region 320. However, a shape of the recovery chamber 300 is not limited thereto. For example, the first and second region 310 and 320 may have a stepped structure as shown in FIG. 10, or the depth of the second region 320 may be smaller than the depth of the first region 310.

The first connecting portion 1112 described above has a rectangular cross-sectional shape, but a cross-sectional shape of the connection portion 1112 is not limited thereto as long as the connection portion 1112 is damaged according to an external force having a predetermined size in order to remove the first lid 410. For example, the first connecting portion 1112 may have a "V" cross-sectional shape.

Figure 11:
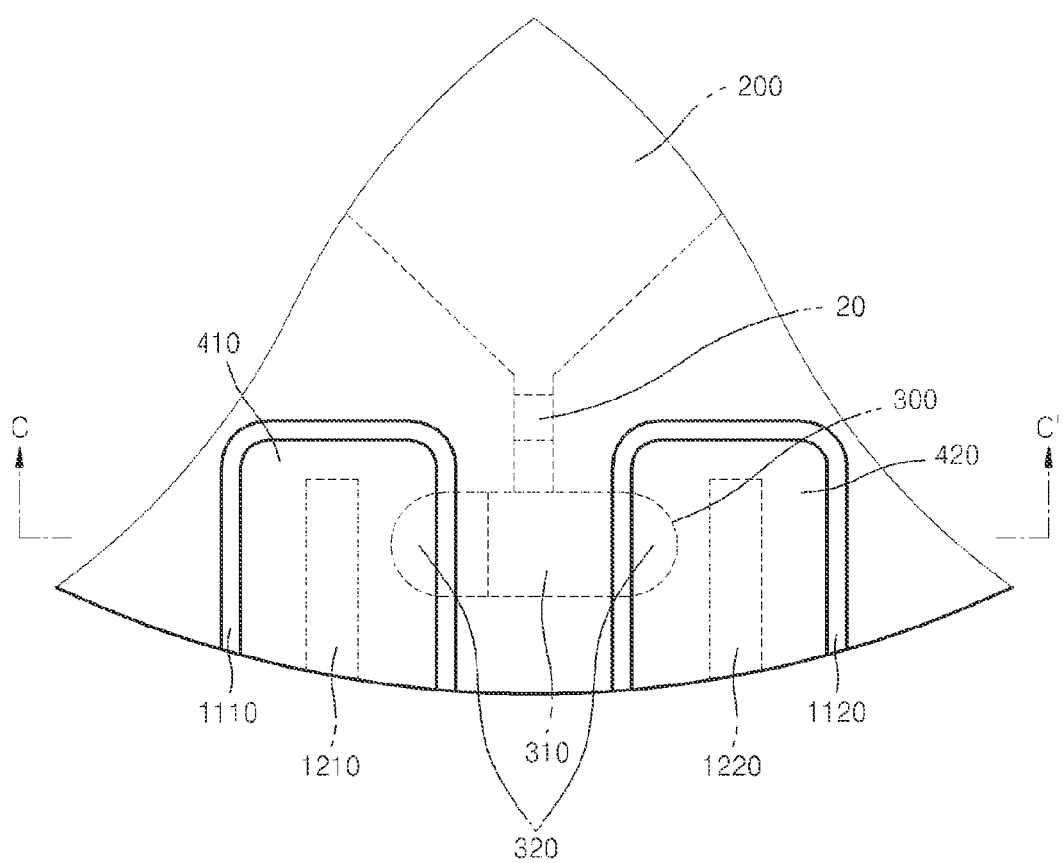
FIG. 11 is a partial plan view of a microfluidic apparatus.
Figure 12:
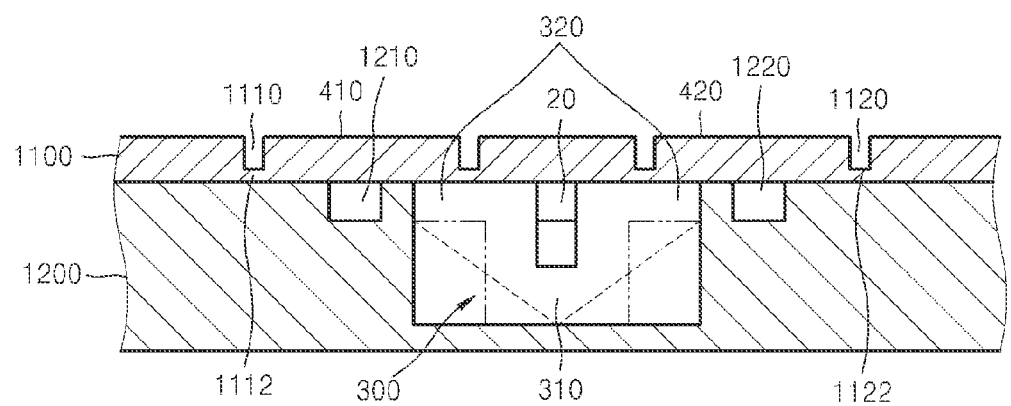
FIG. 12 is a cross-sectional view taken along a line C-C' of FIG. 11.

FIG. 11 is a partial plan view of the microfluidic apparatus 1 according to an embodiment of the present inventive concept. FIG. 12 is a cross-sectional view taken along a line C-C' of FIG. 11, according to an embodiment of the present inventive concept. Referring to FIGS. 11 and 12, first and second lids 410 and 420 opening two locations of the recovery chamber 300 are shown. The first and second lids 410 and 420 are classified from other portions of the upper plate 1100 respectively by first and second grooves 1110 and 1120 depressed downward from the top surface 1101 of the upper plate 1100. The first and second lids 410 and 420 are connected to the upper plate 1100 by first and second connecting portions 1112 and 1122 having thicknesses that are smaller than the thickness of the upper plate and formed by the first and second removal grooves 1110 and 1120. In order to separate the first and second lids 410 and 420, the lower structure 1200 includes first and second depressed portions 1210 and 1220 extending inward along the bottom surfaces of the first and second lids 410 and 420.

In order to reduce a loss of the target material while removing the first and second lids 410 and 420, the first and second lids 410 and 420 are located to open the second region 320 at both sides of the first region 310 in the circumferential direction of the recovery chamber 300. The first lid 410 may be removed from the upper plate 1100 to function as a passage for a pipette for recovering the target material from the recovery chamber 300. The second lid 420 may be removed from the upper plate 1100 to function as an air vent for the pipette. Accordingly, the target material may be easily recovered.

The recovery chamber 300 may have a flat cross-sectional shape as denoted by a solid line, or may have a tilted or stepped shape such that the depth of the second region 320 is smaller than the depth of the first region 310 as denoted by a dashed line or an alternate long and two short dash line.

A method of enriching and separating a target cell using the microfluidic apparatus 1 described above will now be described. In the current embodiment, blood containing circulating cancer cells is used as a sample.

[Preparation]: About 5 mmL of blood containing circulating cancer cells as a target cell and more than about $1 \times 10^8$ of fine beads combined with an antibody that binds specifically to an antigen of the target cell are loaded into the sample chamber 100 through the inlet hole h1. In addition, an appropriately selected DGM is loaded into the separation chamber 200 through the inlet hole h2. The DGM may be Ficoll, Percoll, polysaccharide, or a sodium chloride (NaCl) solution. Since WBCs and circulating cancer cells have similar physical properties, WBCs and circulating cancer cells are isolated in a same layer upon density gradient centrifugation. Thus, in the current embodiment, only cancer cells are separated from the blood by binding the fine beads to the circulating cancer cells to induce a density difference from the WBCs. For example, the fine beads may be melamine particles having a density of about 1.57 g/cm$^3$ that is greater than a density of about 1.05 to about 1.1 g/cm$^3$ of biological particles present in the blood.

[Discharge of Plasma]: As described above, the specific binding of the fine beads and the target cell may depend on an antigen-antibody binding. A sample may contain various kinds of proteins and such proteins may prohibit the specific binding between the fine beads and the target cell. For example, binding between the fine beads and the target cell may be prevented when a protein that has a structure similar to an antigen is bound to a surface marker of the target cell in advance. In addition, binding between the fine beads and the target cell may be prevented when a protein that has a structure similar to an antibody is bound to a ligand of the fine beads. As such, proteins in the sample prevent generation of a target cell-fine beads complex, thereby lowering enrichment efficiency of the target cell. To prevent the decrease in the enrichment efficiency, proteins in the sample may be removed from the sample before the fine beads are mixed with the sample.

In this regard, after the blood containing the circulating cancer cells as a target cell is loaded into the sample chamber 100, the microfluidic apparatus 1 is mounted on the rotation driver 510 and is rotated for about five minutes at a rate of about 1000 to about 8000 rpm, e.g., about 3000 rpm. Then, in the sample chamber 100, the blood is separated into a plurality of layers according to density differences. An RBC layer containing RBCs that are heaviest is located at an outermost portion of the sample chamber 100 in the radial direction. A target layer containing WBCs and the target cell, and a plasma layer as an upper material layer are sequentially arranged next to the RBC layer. Since proteins in the blood excluding blood cells are lighter than the blood cells, the proteins are disposed in the plasma layer. After stopping the microfluidic apparatus 1 from rotating, the electromagnetic wave generator 520 irradiates electromagnetic waves such as laser beams to the discharge valve 35 in order to open the discharge channel 30. Upon rotating the microfluidic apparatus 1 again, plasma is discharged into the waste chamber 110 through the discharge valve 35 according to a centrifugal force. At this time, all or some of the proteins in the blood that may prohibit binding between the target cell and the fine beads are discharged into the waste chamber 110 together with the plasma. Then, the electronic wave generator 520 irradiates electromagnetic waves such as laser beams to the discharge valve 36 in order to close the discharge channel 30.

[Formation of Target Material (Target Cell-Fine Beads Complex)]: The microfluidic apparatus 1 is repeatedly rotated clockwise and counterclockwise for a predetermined time so that the fine beads contact and are bound to the target cell, thereby forming a target material in the sample chamber 100.

[Transporting of Fluid]: The electromagnetic wave generator 520 irradiates electromagnetic waves such as laser beams to the sample valve 15 to open the sample channel 10. Then, the valve material V1 melts and thus the sample channel 10 is opened. According to a centrifugal force generated by rotating the microfluidic apparatus 1, the fluid in the sample chamber 100 is transported to the separation chamber 200 that accommodates the DGM through the sample channel 10.

[Separation of Target Material using Density Gradient within Separation Chamber 200]: The microfluidic apparatus 1 is rotated for about 10 minutes at a rate of, for example, 4000 rpm. Then, in the separation chamber 200, the sample is separated into a plurality of layers according to density gradients of materials in the sample. For example, the sample may be divided into a DGM layer, an RBC layer, a WBC layer, and a plasma layer in the separation chamber 200. Since the target material containing the target cell bonded to the fine beads has the highest density, the target cell is separated from the WBC layer in the form of the target material and is located at a lowermost portion of the separation chamber 200, i.e., an outermost portion in the radial direction based on the rotation center RC. Then, the DGM layer, the RBC layer, the WBC layer, and the plasma layer are sequentially arranged toward the rotational center RC.

[Recovery of Target Material]: Since the recovery valve 25 is opened, the target material located in the lowermost portion of the separation chamber 200 along with the DGM is transported to the recovery chamber 300 through the recovery channel 20. After the target material is transported, energy is supplied to the recovery valve 25 to close the recovery channel 20. Then, the first lid 410 or the first and second lids 410 and 420 are removed from the upper plate 1100, and the target material collected in the recovery chamber 300 is recovered by using a pipette or the like. Since the density and volume of the target material are greater than those of other cells in the blood, it is easy to separate the target material through filtration. Thus, upon subsequent filtration, an enriched target material excluding the fluid may be obtained.

According to the microfluidic apparatus 1 shown in FIGS. 3 through 10, the top of the recovery chamber 300 may be opened by removing the first lid 410. Accordingly, the target material may be effectively recovered by using a pipette or the like. Since the first lid 410 opens the second region 320 of the recovery chamber 300, a loss of the target material may be reduced while removing the first lid 410, and thus a recovery rate of the target material may be increased. By employing the recovery chamber 300 in which the depth of the second region 320 is smaller than the depth of the first region 310, the recovery rate of the target material may be further increased.

According to the microfluidic apparatus 1 shown in FIGS. 11 and 12, by removing the first and second lids 410 and 420 from the upper plate 1100, a passage and an air vent for a pipette are provided, and thus recovering of the target material may be further facilitated.

In the microfluidic apparatus 1, in order to discharge an upper material layer into the waste chamber 110 or to transport the target material into the separation chamber 200 after performing centrifugation to separate the sample in the sample chamber 100 into a plurality of layers according to a density gradient, the microfluidic apparatus 1 may be stopped from rotating and then the discharge valve 35 or the sample valve 15 may be opened. At this time, since the microfluidic apparatus 1 does not rotate, a centrifugal force does not act on the sample in the sample chamber 100, and after some time elapses, the plurality of layers may be gradually mixed together due to molecular motions in the sample. Accordingly, the upper material layer may be mixed with a target layer containing the target cell, thereby decreasing the enrichment efficiency, or discharging the target cell to the waste chamber 110 together with the upper material layer.

Referring to FIG. 2, the sample chamber 100 may include a barrier wall 600 for at least partially restricting a flow of a fluid in the radial direction. The barrier wall 600 may occupy a portion of the width of the sample chamber 100 in a circumferential direction of the sample chamber 100. Alternatively, the barrier wall 600 may occupy the entire width of the sample chamber 100 in the circumferential direction as shown in FIG. 2.

Figure 13:
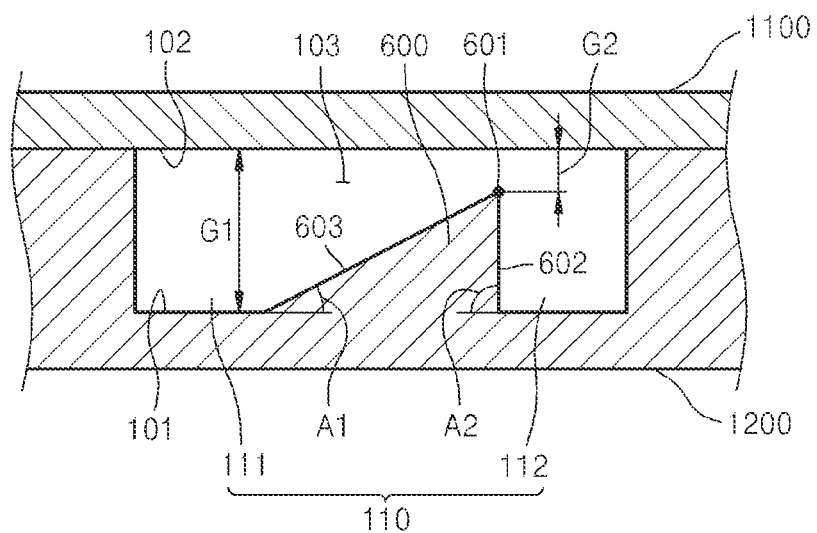
FIG. 13 is a cross-sectional view taken along a line D-D' of FIG. 2.

FIG. 13 is a cross-sectional view taken along a line D-D' of FIG. 2, according to an embodiment of the present inventive concept. Referring to FIG. 13, the barrier wall 600 may extend from a lower wall 101 of the sample chamber 100 toward an upper wall 102 thereof. The sample chamber 100 is divided by the barrier wall 600 into an inner region 111 that is located close to the rotation center RC in the radial direction and an outer region 112 that is located away from the rotation center RC. The barrier wall 600 forms a bottleneck portion 103 with the upper wall 102. The inner region 111 is connected to the outer region 112 by the bottleneck portion 103. Although not shown, the barrier wall 600 may extend from the upper wall 102 of the sample chamber 100 toward the lower wall 101 thereof and to form the bottleneck portion 103 with the lower wall 101.

During the centrifugation of the sample, the sample is moved from the inner region 111 and the outer region 112 across the bottleneck portion 103 according to a centrifugal force, and the sample may be separated into a plurality of layers according to a density gradient within the sample chamber 100. When the microfluidic apparatus 1 is stopped from rotating and the centrifugal force disappears, the bottleneck portion 103 serves to restrict movement of the sample between the inner region 111 and the outer region 112. In other words, the flow of the fluid in the radial direction is restricted by the barrier wall 600 in the sample chamber 100, and thus, mixing of the layers separated from each other by the centrifugation may be reduced or prevented. An inner gap G1 and an outer gap G2 of the bottleneck portion 103 that are distances between the bottom neck portion 103 and the upper wall 102 are greater than a gap inducing a capillary action so as to allow movement of the fluid through the bottleneck portion 103. When the capillary action occurs at the bottleneck portion 103, the bottleneck portion 103 may clog and prohibit movement of the fluid during the centrifugation. In the microfluidic apparatus 1 according to the current embodiment, the inner and outer gaps G1 and G2 of the bottleneck portion 103 are greater than the gap that induces a capillary action, thereby facilitating smooth movement of the fluid from the inner region 111 to the outer region 112 according to a centrifugal force during centrifugation. Furthermore, after the centrifugation, the movement of the fluid between the inner region 111 and the outer region 112 may be partially restricted according to the narrow inner and outer gaps G1 and G2.

It is necessary to facilitate movement of the sample from the inner region 111 to the outer region 112 during the centrifugation. To achieve this, the barrier wall 600 may be formed such that the bottleneck portion 103 becomes narrower from an inner portion of the sample chamber 100 to an outer portion of the sample chamber 100 as shown in FIG. 13. In other words, a path of the fluid formed by the bottleneck portion 103 may have the inner gap G1 wider than the outer gap G2. Since the sample flows from the inner region 111 to the outer region 112 according to a centrifugal force during the centrifugation, the sample may easily pass through the bottleneck portion 103 and then move to the outer region 112 through the wide inner gap G1. On the other hand, when the microfluidic apparatus 1 is stopped from rotating, i.e., in the absence of a centrifugal force, the sample may not easily pass through the bottleneck portion 103 due to the narrow outer gap G2. Thus, such a structure may facilitate movement of the sample from the inner region 111 to the outer region 112 during the centrifugation while limiting the flow of the sample from the outer region 112 to the inner region 111 when the microfluidic apparatus 1 is stopped. The barrier wall 600 for forming the bottleneck portion 103 may have a triangular cross-sectional shape that has an apex 601 as shown in FIG. 13. In this case, a hypotenuse 602 at the outer region 112 has a larger inclination angle A2 than an inclination angle A1 of a hypotenuse 603 at the inner region 111. Accordingly, the flow of the sample from the outer region 112 to the inner region 111 may be further easily restricted. Furthermore, since no stepped portion exists between the hypotenuse 603 and the lower wall 101 of the inner region 111, a smooth flow of the sample from the inner region 111 to the outer region 112 may be further facilitated during the centrifugation.

Figure 14:
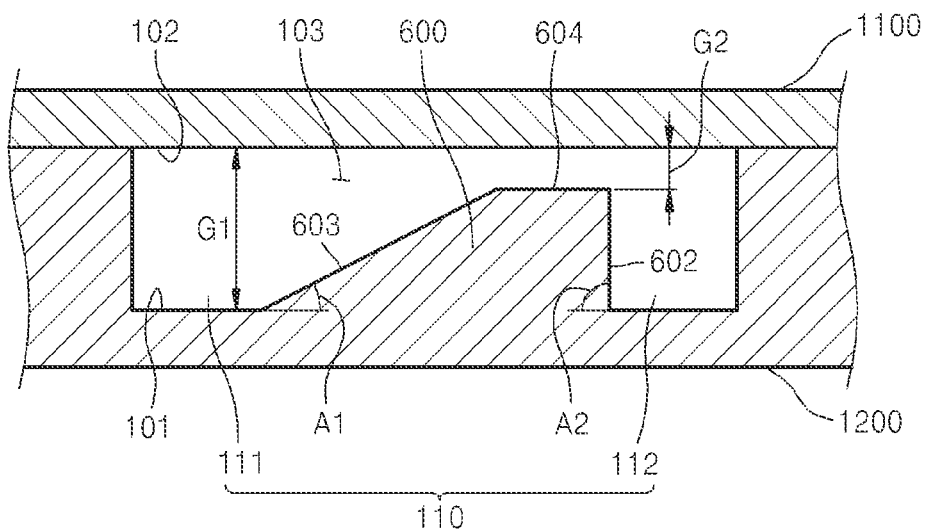
FIG. 14 is a cross-sectional view of a bottleneck portion.

Although the barrier wall 600 has a triangular cross-sectional shape as shown in FIG. 13, a cross-sectional shape of the barrier wall 600 is not limited thereto. Referring to FIG. 14, the barrier wall 600 may have a trapezoidal cross-sectional shape that, together with the bottom surface to which it is attached, has a vertical wall 602 perpendicular to upper wall 102, a hypotenus 603, and a top side 604 parallel to the upper wall 102. Alternatively, the barrier wall 600 may have any one of various cross-sectional shapes as long as a minimum gap of the bottleneck portion 103 is greater than a gap that includes a capillary action.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A microfluidic apparatus that induces a flow of a fluid by centrifugal force when rotated, the microfluidic apparatus comprising:
    a lower structure having a microfluidic structure comprising a separation chamber configured to separate a target material from a sample, a recovery chamber for accommodating the target material separated from the sample, and a recovery channel connecting the separation chamber to the recovery chamber and providing an inflow path of the target material to the recovery chamber; and
    an upper plate providing an upper wall of the recovery chamber and the recovery channel, wherein the upper plate comprises an integrated first lid that is removable from the upper plate to open at least part of the recovery chamber,
    wherein the recovery chamber comprises a first region where the recovery channel connects to the recovery chamber, and a second region that is adjacent to the first region in a direction along a circumference of the microfluidic apparatus, and
    the first lid covers the second region but not the first region.

2. The microfluidic apparatus of claim 1, wherein the upper plate comprises a removal groove depressed into the upper plate from at least one of a top surface or a bottom surface of the upper plate, the removal groove defining an edge of the first lid, and
    the first lid can be separated from the upper plate along the removal groove.

3. The microfluidic apparatus of claim 2, wherein a part of the edge of the first lid is exposed along an outer perimeter of the microfluidic apparatus.

4. The microfluidic apparatus of claim 3, wherein the lower structure comprises a depressed portion in an outer perimeter of the lower structure adjacent to the exposed part of the edge of the first lid, the depressed portion extending along a bottom surface of the first lid.

5. The microfluidic apparatus of claim 1, wherein a depth of the second region is smaller than a depth of the first region.

6. The microfluidic apparatus of claim 5, wherein a depth of the recovery chamber decreases from the first region to the second region.

7. The microfluidic apparatus of claim 1, wherein the upper plate further comprises an integrated second lid, and wherein the first lid and second lid are spaced apart from each other.

8. The microfluidic apparatus of claim 7, wherein
    the first and second lids cover the second region but not the first region.

9. The microfluidic apparatus of claim 1, wherein a depth of the recovery chamber decreases from the first region to the second region.

10. The microfluidic apparatus of claim 7, wherein the second lid is positioned to cover only the second region.

11. The microfluidic apparatus of claim 10, wherein a depth of the second region is smaller than a depth of the first region.

12. The microfluidic apparatus of claim 1, further comprising:
    a sample chamber in which fine beads are adhered to a target cell in the sample to form the target material;
    the separation chamber accommodating a density gradient medium having a lower density than the target material, receiving a fluid including the target material from the sample chamber, and separating the target material from the fluid according to a density difference; and
    a sample channel connecting the sample chamber to the separation chamber.

13. The microfluidic apparatus of claim 7, wherein the upper plate comprises first and second removal grooves defining the first and second lids, the removal grooves being depressed into the upper plate from at least one of a top surface or a bottom surface of the upper plate such that the first and second lids are integrally formed with the upper plate, and the first and second lids can be separated from the upper plate along the first and second removal grooves.

14. The microfluidic apparatus of claim 13, wherein a part of the edge of each of the first and second lids is exposed along an outer perimeter of the microfluidic apparatus.

15. The microfluidic apparatus of claim 14, the lower structure comprises depressed portions in an outer perimeter of the lower structure adjacent to the exposed part of the edge of each of the first and second lids, the depressed portions extending along a bottom surfaces of the first and second lids.

16. A method of isolating a target material from a sample comprising introducing a sample comprising a target material into a microfluidic apparatus of claim 1, and rotating the apparatus to induce a flow of fluid by centrifugal force, whereby the target material is isolated in the recovery chamber of the apparatus, optionally wherein the target material is a target cell, a circulating tumor cell, a cancer stem cell, or a cancer cell.

17. The microfluidic apparatus of claim 1, wherein the first region has a width in the circumferential direction that is equal to or greater than the width of the recovery channel connected to the first region.

\* \* \* \* \*